United States Patent
Meyers et al.

(10) Patent No.: US 11,763,456 B2
(45) Date of Patent: Sep. 19, 2023

(54) SYSTEMS AND METHODS FOR PROCESSING ECHOCARDIOGRAM IMAGES

(71) Applicant: Purdue Research Foundation, West Lafayette, IN (US)

(72) Inventors: Brett Albert Meyers, West Lafayette, IN (US); Pavlos P. Vlachos, West Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 41 days.

(21) Appl. No.: 17/199,017

(22) Filed: Mar. 11, 2021

(65) Prior Publication Data
US 2021/0287371 A1 Sep. 16, 2021

Related U.S. Application Data

(60) Provisional application No. 62/987,964, filed on Mar. 11, 2020.

(51) Int. Cl.
| | |
|---|---|
| *G06T 7/00* | (2017.01) |
| *G06T 7/246* | (2017.01) |
| *G06T 7/33* | (2017.01) |
| *G06T 3/00* | (2006.01) |
| *G06T 7/37* | (2017.01) |
| *A61B 8/08* | (2006.01) |

(52) U.S. Cl.
CPC ............ *G06T 7/0014* (2013.01); *A61B 8/485* (2013.01); *A61B 8/5223* (2013.01); *G06T 3/0006* (2013.01); *G06T 7/246* (2017.01); *G06T 7/337* (2017.01); *G06T 7/37* (2017.01); *A61B 8/0883* (2013.01); *G06T 2207/20056* (2013.01); *G06T 2207/20101* (2013.01); *G06T 2207/20132* (2013.01); *G06T 2207/30048* (2013.01)

(58) Field of Classification Search
None
See application file for complete search history.

(56) References Cited

U.S. PATENT DOCUMENTS

| | | | | |
|---|---|---|---|---|
| 9,629,615 | B1* | 4/2017 | Tavakoli | A61B 8/5246 |
| 2002/0072670 | A1* | 6/2002 | Chenal | A61B 8/0883 |
| | | | | 600/449 |
| 2002/0072671 | A1* | 6/2002 | Chenal | G06T 7/12 |
| | | | | 600/450 |
| 2008/0095417 | A1* | 4/2008 | Pedrizzetti | A61B 8/483 |
| | | | | 382/128 |

(Continued)

OTHER PUBLICATIONS

Anderson et al., Beginner's Guide to Strain: What should be in your lab in 2018, 2018, asecho.org/wp-content/uploads/2018/01/Anderson-Beginners-Guide-to-Strain.pdf, pp. 1-18.*

(Continued)

*Primary Examiner* — Guillermo M Rivera-Martinez
(74) *Attorney, Agent, or Firm* — Purdue Research Foundation

(57) ABSTRACT

The present application includes a method and a software architecture for measuring global longitudinal strain (GLS) and global longitudinal strain rate (GLSr) from 2D echocardiograms. In contrast to conventional GLS computation methods, this approach does not require boundary segmentation and regularization.

10 Claims, 6 Drawing Sheets

(56) References Cited

U.S. PATENT DOCUMENTS

| | | | | |
|---|---|---|---|---|
| 2015/0133802 | A1* | 5/2015 | Nabutovsky | A61B 5/0245 600/508 |
| 2015/0206323 | A1* | 7/2015 | Lee | A61B 8/485 382/107 |
| 2016/0098833 | A1* | 4/2016 | Tsadok | G06T 7/38 382/128 |
| 2017/0065242 | A1* | 3/2017 | Chirvasa | A61B 6/466 |
| 2019/0125309 | A1* | 5/2019 | Ramm | A61B 5/352 |
| 2019/0205478 | A1 | 7/2019 | Cavallo et al. | |
| 2019/0328364 | A1* | 10/2019 | Questa | A61B 8/485 |
| 2020/0193603 | A1 | 6/2020 | Golden et al. | |
| 2021/0100526 | A1* | 4/2021 | Schein | A61B 8/085 |

OTHER PUBLICATIONS

Becker et al., Analysis of myocardial deformation based on pixel tracking in two dimensional echocardiographic images enables quantitative assessment of regional left ventricular function, 2006, pp. 1102-1108.*

Biering-Sørensen et al., Global Longitudinal Strain by Echocardiography Predicts Long-Term Risk of Cardiovascular Morbidity and Mortality in a Low-Risk General Populatio The Copenhagen City Heart Study, 2017, DOI: 10.1161/CIRCIMAGING.116.005521, pp. 1-11.*

Karlsen et al., Global longitudinal strain is a more reproducible measure of left ventricular function than ejection fraction regardless of echocardiographic training, 2019, doi: 10.1186/s12947-019-0168-9, pp. 1-12.*

Chan ety al., Left ventricular Global-Strain Analysis by Two Dimensional Speckle Tracking Echocardiography, 2017, asecho.org/wp-content/uploads/2021/10/Left-Ventricular-Global-Strain-Analysis-by-Two-Dimensional-Speckle-Tracking-Echocardiography_-The-Learning-Curve-PIIS0894731717304698.pdf, pp. 1081-1090.*

Pedrizzetti et al., Principles of cardiovascular magnetic resonance feature tracking and echocardiographic speckle tracking for informed clinical use, 2016, Pedrizzetti et al. Journal of Cardiovascular Magnetic Resonance (2016) 18:51, DOI 10.1186/s12968-016-0269-7, pp. 1-12.*

Alessandrini, M. et al., A Pipeline for the Generation of Realistic 3D Synthetic Echocardiographic Sequences: Methodology and Open-Access Database, IEEE Transactions on Medical Imaging, 34(7), pp. 1436-1451, 2015.

Alessandrini, M. et al., Generation of Ultra-realistic Synthetic Echocardiographic Sequences to Facilitate Standardization of Deformation Imaging, in 2015 IEEE 12th International Symposium on Biomedical Imaging (ISBI), vol. Jul. 2015, No. September, pp. 756-759, 2015.

Bell, M.A.L. et al., Short-lag Spatial Coherence Imaging of Cardiac Ultrasound Data: Initial Clinical Results, Ultrasound in Med. & Biol., 39(10), pp. 1861-1874, 2013.

D'Hooge, J. et al., Two-dimensional speckle tracking echocardiography: standardization efforts based on synthetic ultrasound data, European Heart Journal—Cardiovascular Imaging, 17(6), pp. 693-701, 2016.

Eckstein, A. et al., Phase correlation processing for DPIV measurements, Exp Fluids, 45, pp. 485-500, 2008.

Eckstein, A. et al., Assessment of advanced windowing techniques for digital particle image velocimetry (DPIV), Measurement Science and Technology, 20(7), 075402 (9 pp), 2009.

Eckstein, A. et al., Digital particle image velocimetry (DPIV) robust phase correlation, Measurement Science and Technology, 20(5), 055401 (14 pp), 2009.

Farsalinos, K.E. et al., Head-to-Head Comparison of Global Longitudinal Strain Measurements among Nine Different Vendors: The EACVI/ASE Inter-Vendor Comparison Study, Journal of the American Society of Echocardiography, 28(10), pp. 1171-1181, 2015.

Meyers, B.A. et al., Development and Validation of a Phase-Filtered Moving Ensemble Correlation for Echocardiographic Particle Image Velocimetry, Ultrasound in Med. & Biol., 44(2), pp. 477-488, 2018.

Mirea, O. et al., Intervendor Differences in the Accuracy of Detecting Regional Functional Abnormalities: A Report from the EACVI-ASE Strain Standardization Task Force, JACC: Cardiovascular Imaging, 11(1), pp. 25-34, 2018.

Mirea, O. et al., Variability and Reproducibility of Segmental Longitudinal Strain Measurement: A Report from the EACVI-ASE Strain Standardization Task Force, JACC: Cardiovascular Imaging, 11(1), pp. 15-24, 2018.

Sarvaiya, J.N. et al., Image Registration Using Log Polar Transform and Phase Correlation to Recover Higher Scale, Journal of Pattern Recognition Research, 7, pp. 90-105, 2012.

Thomas, J.D. et al., EACVI-ASE-industry initiative to standardize deformation imaging: a brief update from the co-chairs, European Heart Journal—Cardiovascular Imaging, 14(11), pp. 1039-1040, 2013.

* cited by examiner to Fig. 1C to Fig. 1E to Fig. 1F

SYSTEMS AND METHODS FOR PROCESSING ECHOCARDIOGRAM IMAGES

CROSS-REFERENCE TO RELATED APPLICATIONS

The present U.S. patent application is related to and claims the priority benefit of U.S. Provisional Patent Application Ser. No. 62/987,964, filed Mar. 11, 2020, the contents of which is hereby incorporated by reference in its entirety into this disclosure.

BACKGROUND

Ejection Fraction (EF) is a standard metric for evaluating left ventriclar (LV) systolic function, assessing heart failure, and tracking outcomes of implantable device surgeries as well as cardiac resynchronization therapy (CRT). However, EF is susceptible to large intra- and inter-observer variation, is load- and age-dependent, and does not characterize diastolic function.

In contrast to EF, Speckle Tracking Echocardiography (STE) strain and strain rate measurements can provide information on diastolic function, while maintaining better sensitivity and differentiation in assessing LV function and heart failure. However, conventional factors, along with user-variability, represent limitations that hinder the establishment of standard ranges for normal and abnormal function for GLS measurements.

SUMMARY

One aspect of the present application relates to a non-transitory machine readable storage medium having a software architecture stored therein, wherein a software architecture is encoded on the non-transitory machine readable storage medium, the software architecture includes a first protocol, wherein the first protocol is configured to read a plurality of images. The software architecture also includes a second protocol, wherein the second protocol is configured to select a set of user defined feature points. The software architecture further includes a third protocol, wherein the third protocol is configured to track the user defined feature points through the plurality of images, thereby yielding a plurality of tracked feature points.

Moreover, the software architecture includes a fourth protocol, wherein the fourth protocol is configured to register the plurality of images to a reference image using the plurality of tracked feature points, thereby yielding a second set of plurality of images. Next, the software architecture includes a fifth protocol, wherein the fifth protocol is configured to crop the second set of plurality of images, thereby yielding a third set of plurality of images, wherein the cropping is user-defined.

Further, the software architecture includes a sixth protocol, wherein the sixth protocol is configured to apply a weight to image pixel intensities of the third set of plurality of images, thereby yielding a fourth set of plurality of images. Moreover, the software architecture includes a seventh protocol, wherein the seventh protocol is configured to perform a transformation on the fourth set of plurality of images from a signal space to a frequency space, thereby yielding transformed set of plurality of images.

The software architecture also includes an eighth protocol, wherein the eighth protocol is configured to compute a magnitude of each image of the transformed set of plurality of images, thereby yielding a set of magnitude transformed images. The software architecture next includes a ninth protocol, wherein the ninth protocol is configured to perform a coordinate transformation on the set of magnitude transformed images, thereby yielding a set of coordinate transformed images. Additionally, the software architecture includes a tenth protocol, wherein the tenth protocol is configured to quantify displacement between pairs of coordinate transformed images, thereby yielding a plurality of displacements across the set of coordinate transformed images.

Next, the software architecture includes an eleventh protocol, wherein the eleventh protocol is configured to transform the plurality of displacements into a Cartesian coordinate system, thereby yielding transformed plurality of displacements. Further, the software architecture includes a twelfth protocol, wherein the twelfth protocol is configured to compute strain rates from the transformed plurality of displacements. Additionally, the software architecture includes a thirteenth protocol, wherein the thirteenth protocol is configured to evaluate strain by integrating the strain rates.

Another aspect of the present application relates to a non-transitory machine readable storage medium having a machine readable program stored therein, wherein the machine readable program, when executed on a processing system, causes the processing system to perform a method of image processing, wherein the method includes reading a plurality of images. The method additionally includes selecting a set of user defined feature points. Further, the method includes tracking the user defined feature points through the plurality of images, thereby yielding a plurality of tracked feature points. Next, the method includes registering the plurality of images to a reference image using the plurality of tracked feature points, thereby yielding a second set of plurality of images.

Moreover, the method includes cropping the second set of plurality of images, thereby yielding a third set of plurality of images, wherein the cropping is user defined. Further, the method includes applying a weight to image pixel intensities of the third set of plurality of images, thereby yielding a fourth set of plurality of images. Next, the method includes performing a transformation on the fourth set of plurality of images from a signal space to a frequency space, thereby yielding transformed set of plurality of images.

The method also includes computing a magnitude of each image of the transformed set of plurality of images, thereby yielding a set of magnitude transformed images. Next, the method includes performing a coordinate transformation on the set of magnitude transformed images, thereby yielding a set of coordinate transformed images. Further, the method includes quantifying displacement between pairs of coordinate transformed images, thereby yielding a plurality of displacements across the set of coordinate transformed images.

Further, the method includes transforming the plurality of displacements into a Cartesian coordinate system, thereby yielding transformed plurality of displacements. Next, the method includes computing strain rates from the transformed plurality of displacements. The method also includes evaluating strain by integrating the strain rates.

BRIEF DESCRIPTION OF THE DRAWINGS

One or more embodiments are illustrated by way of example, and not by limitation, in the figures of the accompanying drawings, wherein elements having the same reference numeral designations represent like elements throughout. It is emphasized that, in accordance with standard practice in the industry, various features may not be drawn to scale and are used for illustration purposes only. In fact, the dimensions of the various features in the drawings may be arbitrarily increased or reduced for clarity of discussion.

DETAILED DESCRIPTION

Figure 1A:
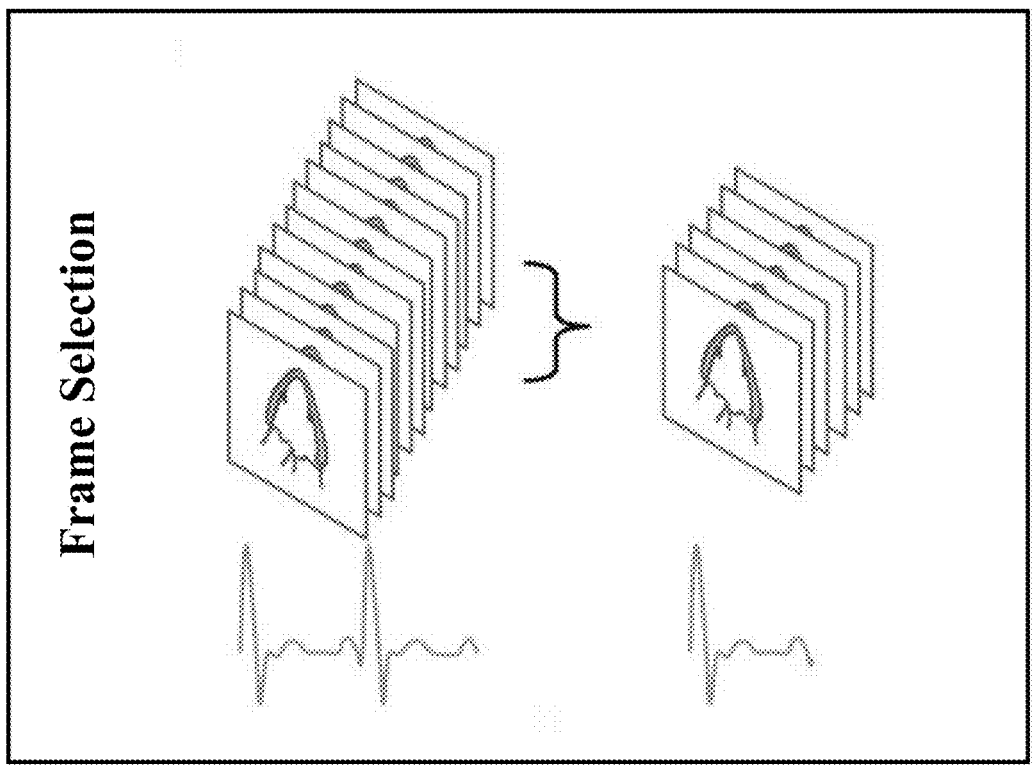
FIGS. 1A-1H collectively depict a flowchart of one exemplary direct longitudinal strain estimation algorithm for measuring global longitudinal strain.

The following disclosure provides many different embodiments, or examples, for implementing different features of the present application. Specific examples of components and arrangements are described below to simplify the present disclosure. These are examples and are not intended to be limiting. The making and using of illustrative embodiments are discussed in detail below. It should be appreciated, however, that the disclosure provides many applicable concepts that can be embodied in a wide variety of specific contexts. In at least some embodiments, one or more embodiment(s) detailed herein and/or variations thereof are combinable with one or more embodiment(s) herein and/or variations thereof.

Various embodiments of the present application relate to a method for direct GLS estimation from echocardiogram recordings, developed to address limitations observed in conventional STE algorithms. The present framework bypasses existing STE limitations including biases due to regional smoothing as well as assumptions on tissue shape and deformation. The method using a logarithm-scale basis transform of the magnitude of Fourier-transformed images.

Throughout the cardiac cycle the LV contracts and relaxes, resulting in motion that is complex and three dimensional. This motion is composed of a planar translation $\vec{T}$ and deformation gradient tensor F which relates the change in position of cardiac tissue from its original position $(x_n, y_n, z_n)$ to its new position $(x_{n+1}, y_{n+1}, z_{n+1})$ [20], $$\begin{bmatrix} x_{n+1} \\ y_{n+1} \\ z_{n+1} \end{bmatrix} = F \begin{bmatrix} x_n \\ y_n \\ z_n \end{bmatrix} + \vec{T} = \begin{bmatrix} a_{11} & a_{12} & a_{13} \\ a_{21} & a_{22} & a_{23} \\ a_{31} & a_{32} & a_{33} \end{bmatrix} \begin{bmatrix} x_n \\ y_n \\ z_n \end{bmatrix} + \begin{bmatrix} t_x \\ t_y \\ t_z \end{bmatrix}. \quad (1)$$

F is homogeneous and is related to the displacement gradient tensor $\nabla u$ through the expression, $$F = I - \nabla u, \quad (2)$$

where I is the identity matrix. Lagrange strain, $\varepsilon$, can be expressed as a function of $\nabla u$ when motion and deformation are small, such that, $$\varepsilon = \frac{1}{2}(\nabla u + \nabla u^T), \quad (3)$$

and the strain when $\varepsilon$ is aligned in the direction of the length change, or the direction of principle stretch, is equivalent to, $$\varepsilon = \frac{l - l_0}{l_0}. \quad (4)$$

Therefore, F is directly related to strain.

For echocardiogram recordings with sufficient frame rates, changes in the speckle patterns between consecutive frames due to elevational motion minimizes compared to the planar motion, allowing motion to be represented in 2D. In the following sections we derive how strain is directly estimated from the cross-correlation of two consecutive frames based on these equations.

Digital image cross-correlation provides a statistical estimate of rigid translation between two images. This estimate is used in applications such as image registration, speckle tracking, particle image velocimetry (PIV), and DIC. The 2D discrete spatial cross-correlation kernel between two consecutive images, $I_n$ and $I_{n+1}$, is expressed as, $$R(x, y) = \sum_{i=-N/2}^{N/2} \sum_{j=-M/2}^{M/2} I_n(i, j) I_{n+1}(x+i, y+j), \quad (5)$$

where R(x, y) is the correlation plane, (i,j) are the summation indices for each pixel intensity, and N and M are the height and width for a neighbourhood, of pixels, respectively. The 2D discrete cross-correlation can be performed in the spectral domain, with the spectral cross-correlation written as, $$R(x,y) = \mathcal{F}^{-1}[\mathcal{F}(I_n(x,y))\mathcal{F}(I_{n+1}(x,y))], \quad (6)$$

where $\mathcal{F}$ is the 2D Fourier transformation (FT).

The affine theorem for Fourier transforms dictates that rotation, stretch, and shear between images will also occur on both the magnitude and phase of the image FT. We can observe how the affine transform contributes to the rigid translation estimate from the cross correlation by replacing $I_{n+1}$ with the relationship defined in Equation 1 for $I_n$, $$R(x,y) = \mathcal{F}^{-1}[\mathcal{F}(I_n(x,y))\mathcal{F}(I_n(x',y'))], \quad (7)$$

which can also be written as, $$R(x, y) = \int \int \frac{\overline{G(u, v)} G(u', v')}{\Delta} e^{-j2\pi(u'(t_1+x)+v'(t_2+y))} du dv. \quad (8)$$

Here, (u, v) are wavenumbers proportional to the positions (x, y), G (u, v) are the FTs, $u' = a_{11}u + a_{21}v$, $v' = a_{12}u + a_{22}v$, and $\Delta = \det(F)$. Equation 8 indicates that the column and row displacements, dy and dx, from the correlation plane peak are translations affected by local displacement gradients, and written as, $$dx = a_{11}t_1 + a_{12}t_2, dy = a_{21}t_1 + a_{22}t_2. \quad (9)$$

The displacement gradients present in the rigid translation estimates in Equation 9 are integral to computing GLS in the conventional algorithms. If translation for all LV image pixel positions are identical, rigid body motion without deformation, or strain, occurs. Strain is only present when translation varies for all LV image pixel positions.

Based on Equation 8, it can be reasoned that the components introduced by F can be observed independent of $\vec{T}$ by separating the FT magnitude, |F(u, v)|, from the phase content. The FT magnitudes of two images can be cross-correlated, where the returned row and column displacements from the cross-correlation plane are a combination of terms from F with no contribution from $\vec{T}$. This correlation method is therefore considered translation invariant. A basis transformation can be used to further decouple terms from F and resolve information on rotation and image stretching.

The Fourier-Mellin transform (FMT) is the most well-known FT magnitude transformation, applying a log-polar basis change to decouple rotation from isotropic scaling. The FT magnitude image coordinates are changed from the Cartesian (u, v) coordinates to orthogonal (log ρ, θ) coordinates. In this coordinate system, the shift theorem indicates the correlation peaks displacements are due to a rotation α and a scale change m such that, $$F(\log \rho + \log m, \theta + \alpha). \quad (10)$$

Using cross-correlation of two FT magnitude image pairs, where one image has undergone a uniform rescaling and rotation to produce the second, allows α and m to be estimated from the row and column displacements. The translation invariance allows rotation and scaling to be estimated reliably, even when a shift is present. The FMT works well when scaling is uniform ($m \propto a_{11} = a_{22}$) and rotation occurs without shear ($\alpha \propto a_{12} = a_{21}$). Therefore, this transform will not work reliably when scaling change is anisotropic.

When scaling is anisotropic a logarithm scale basis change should be used. Changing the FT magnitude image coordinates from cartesian (u, v) to orthogonal (log u, log v) coordinates results in the shift theorem introducing displacements due to horizontal rescaling a and vertical rescaling b such that, $$F(\log u + \log a, \log v + \log b). \quad (11)$$

Rescaling is still reliably estimated although the translation invariance allows a shift to be present. This transform does require that rotation and shear be minimized (observed from the terms present in Equation 8. The row and column displacements estimate a and b are related to the terms $a_{11}$ and $a_{22}$ from F through, $$a_{11} \cong e^{dy}, a_{22} \cong e^{dx} \quad (12)$$

Our algorithm for computing LV GLS from B-mode ultrasound scans uses Fourier-based cross-correlation of the logarithm scale image FT magnitudes to estimate the stretch that takes place along the length of the ventricle. As long as rotation and shear are assumed negligible (or minimized), $a_{11}$ and $a_{22}$ from Equation 12 can replace F in Equation 2 which can then be used to solve for $\nabla u$ such that, $$\nabla u = \begin{bmatrix} e^{dx} - 1 & 0 \\ 0 & e^{dy} - 1 \end{bmatrix}. \quad (13)$$

Because most of the deformation in the scans occurs along the length of the ventricle, we assume GLS occurs predominantly along the vertical direction; thus, GLS can be estimated as, $$\varepsilon_{GLS} = \frac{l - l_0}{l_0} \approx e^{dy} - 1. \quad (14)$$

FIGS. 1A-1H show a flowchart, through a series of schematics, of one algorithm to compute global longitudinal strain (GLS) based on the correlation of logarithm scale FT magnitudes. The algorithm is composed of two general stages: the first stage performs an image registration to minimize shear, rotation, and noise that can corrupt the correlation accuracy, while the second stage performs GLS estimation.

Figure 1B:
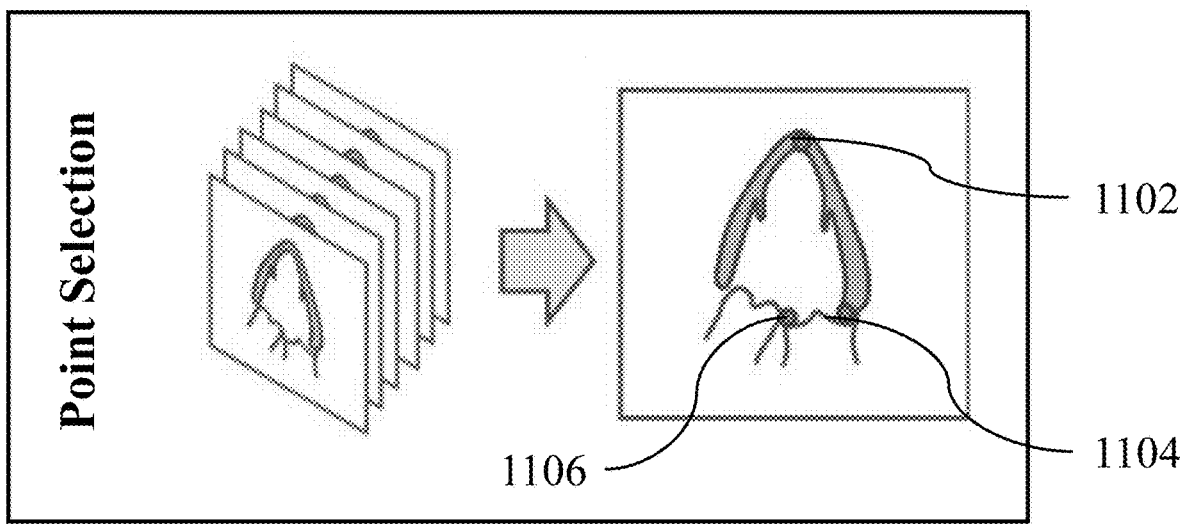
Figure 1C:
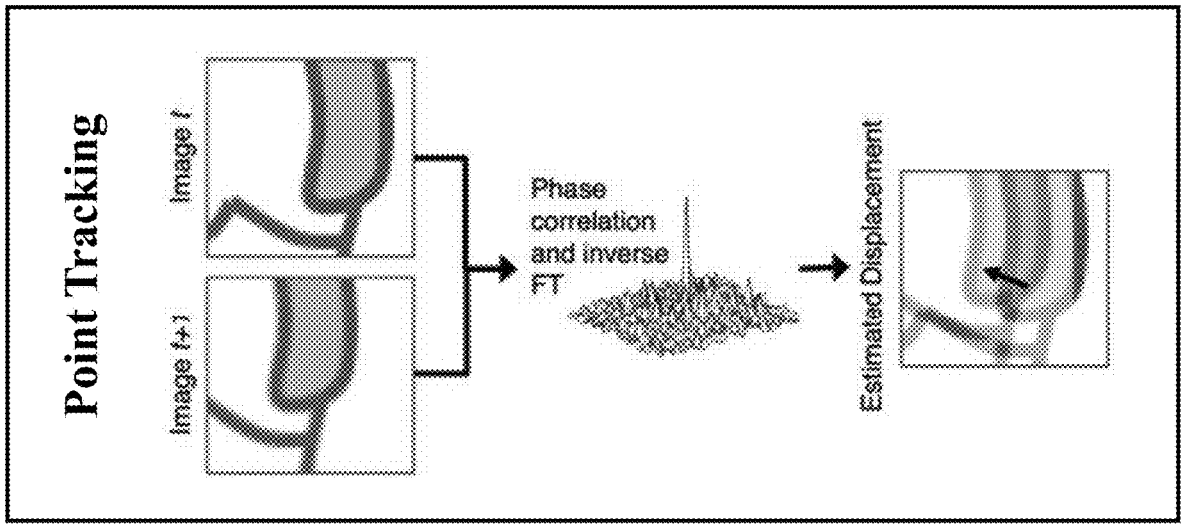
Figure 1D:
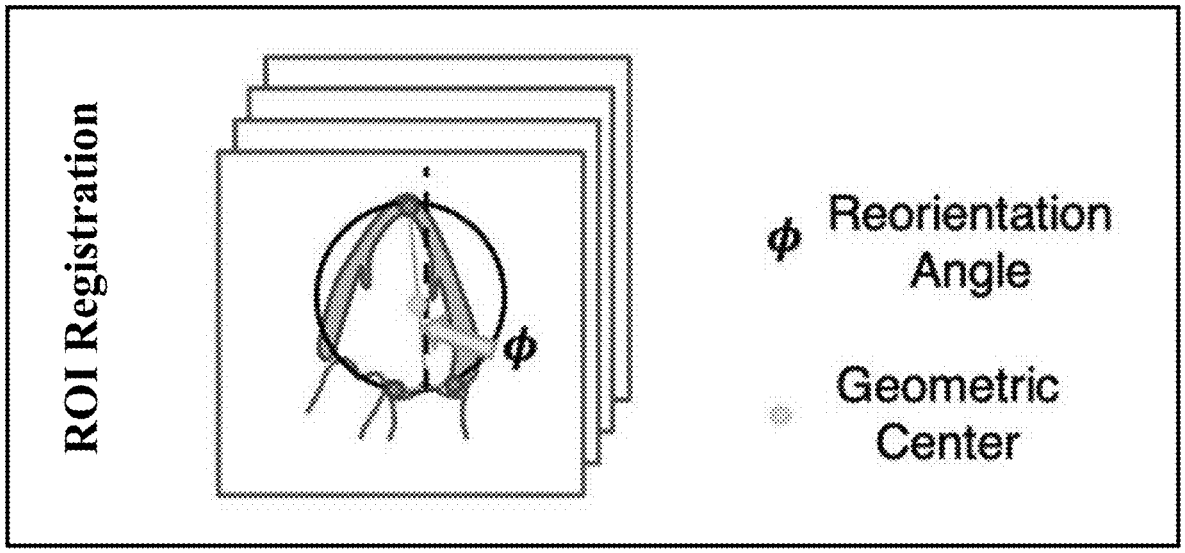

In the first general stage, the algorithm begins with the user selecting the frames across a single heartbeat from peak diastole to peak diastole (R-R interval), as shown in FIG. 1A. Next, as shown in FIG. 1B, three initial points (1102, 1104, 1106) from the first frame in the stack are selected, corresponding to the LV apex, the mitral annulus (M A) septal, and the MA lateral positions. As shown in FIG. 1C, these points (1102, 1104, 1106) are then tracked between consecutive frames using standard pairwise cross-correlation. As shown in FIG. 1D, for each frame, the geometric center from the tracked points (1102, 1104, 1106) is computed with the orientation angle from the vertical axis, for a line formed from the MA center to the apex. Frames are aligned with the geometric center set to the image midpoint. The orientation angle from vertical is corrected. A circular ROI is then resolved from the tracked points for each frame and used to remove tissue signal and noise that occurs outside the LV.

Figure 1E:
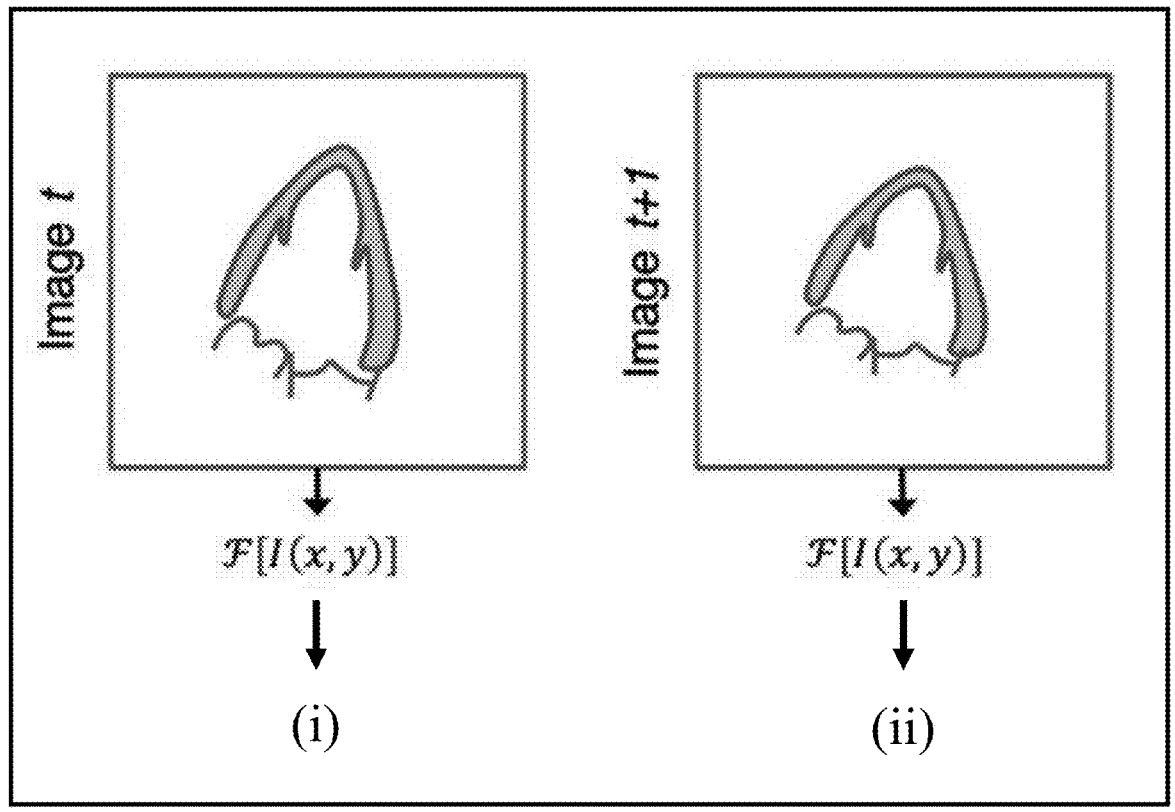
Figure 1F:
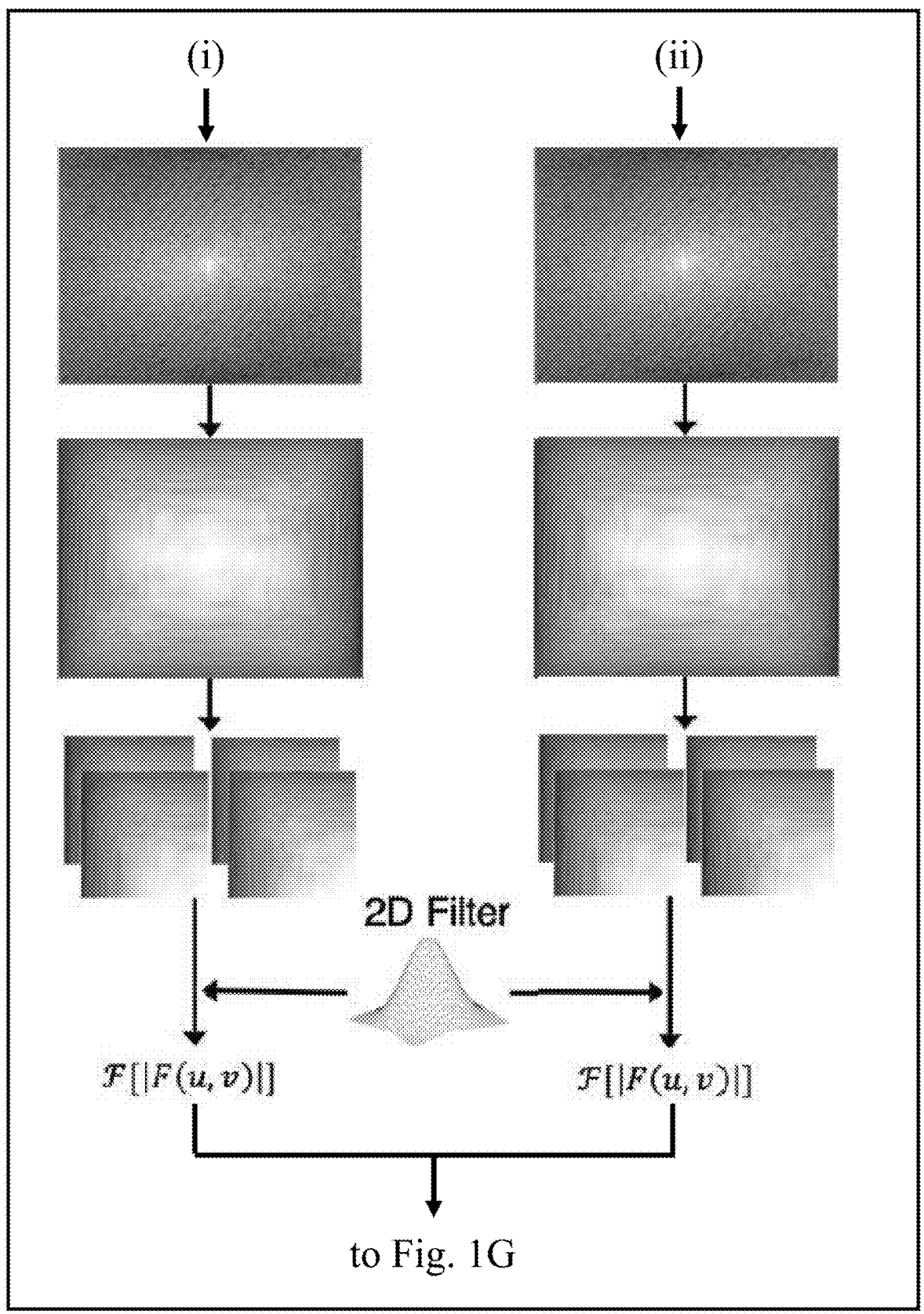
Figure 1G:
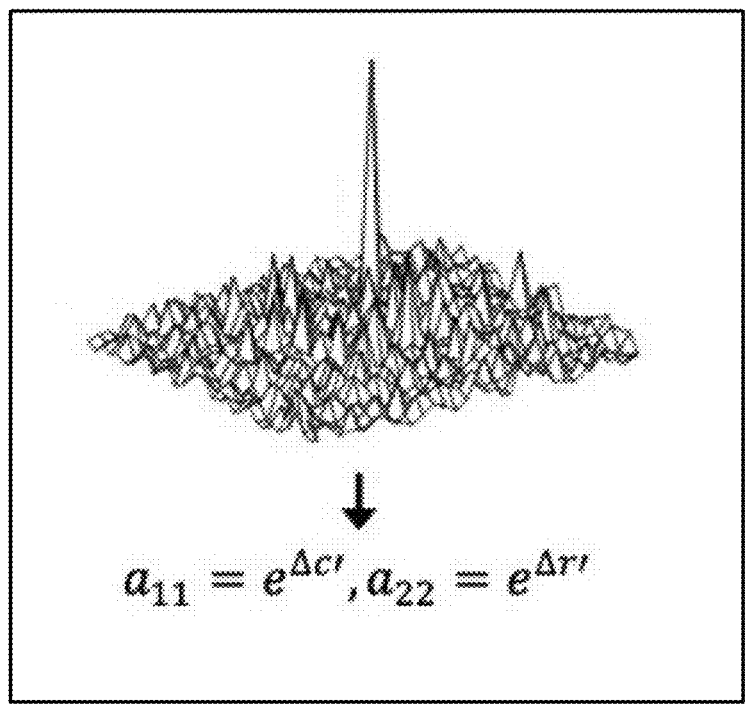
Figure 1H:
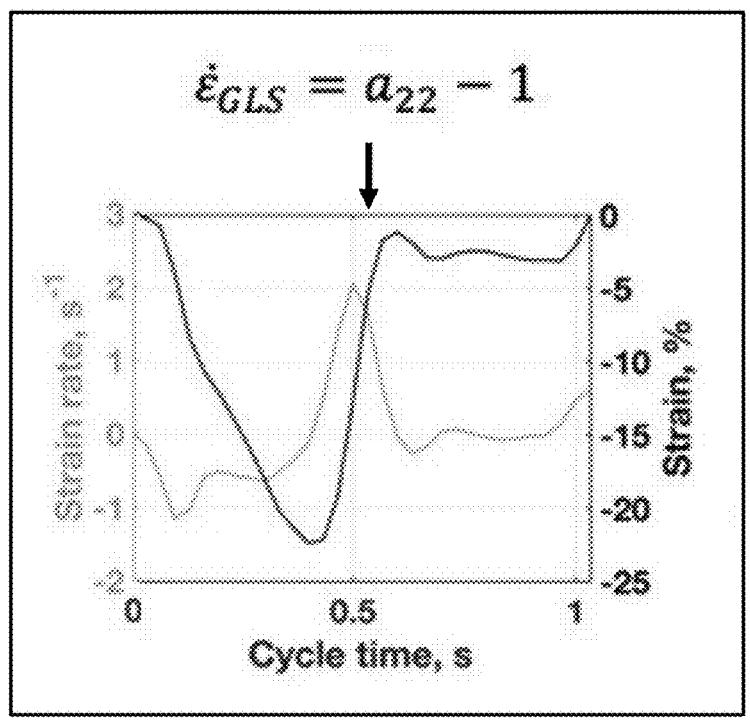
Figure 2:
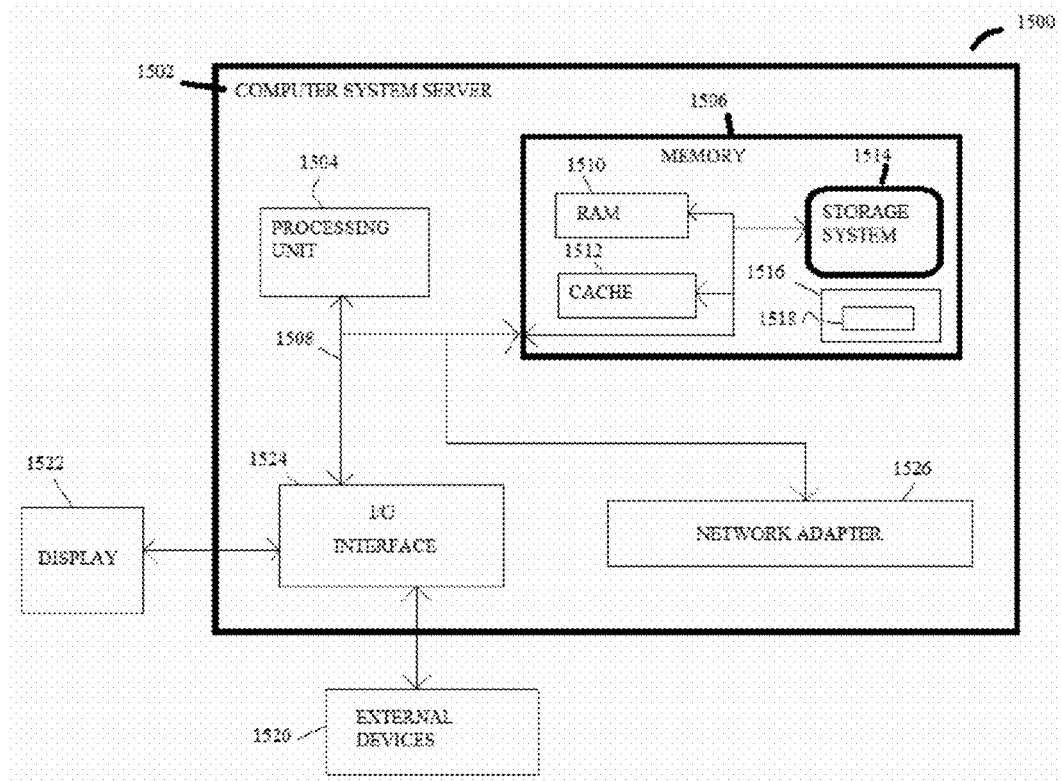
FIG. 2 depicts a block diagram of one example of a computing or processing node 1500 for executing the method or the software architecture of the present application.

In the second general stage, for a pair of sequential registered images, t and t+1, as shown in FIG. 1E, the FT for each image and their FT magnitude is computed. The FT magnitudes are then interpolated from the image grid onto a logarithm-scale grid, as shown in FIG. 1F. To properly estimate the stretch through cross-correlation, the FT logarithm transform images may be separated into four quarters. This is because the horizontal stretch between the left and right side of the images can have the same magnitude but of opposite sign. The same occurs for the vertical stretch between the top half and bottom half of the images. After the images are separated, each sub-image is filtered, and the FT computed. As shown in FIG. 1G, the FT sub-images from the frame pair are then correlated using the spectral cross-correlation kernel to provide the row and column displacements Δr and Δc. A dynamic phase-filtered kernel is applied to the cross-correlation to improve estimate accuracy. The displacements Δr and Δc are adjusted based on the logarithm-scale grid, becoming Δr' and Δc'. The global longitudinal strain rate (GLSr) between the frame pair is computed using Δr, from Equation 14 above. Finally, as shown in FIG. 1H, GLSr across each frame pair is integrated in time using 4th-order Runge-Kutta to obtain GLS.

Example 1

A non-transitory machine readable storage medium having a software architecture stored therein, wherein a software architecture is encoded on the non-transitory machine readable storage medium, the software architecture includes a first protocol, wherein the first protocol is configured to read a plurality of images. The software architecture also includes a second protocol, wherein the second protocol is configured to select a set of user defined feature points. The software architecture further includes a third protocol, wherein the third protocol is configured to track the user defined feature points through the plurality of images, thereby yielding a plurality of tracked feature points.

Moreover, the software architecture includes a fourth protocol, wherein the fourth protocol is configured to register the plurality of images to a reference image using the plurality of tracked feature points, thereby yielding a second set of plurality of images. Next, the software architecture includes a fifth protocol, wherein the fifth protocol is configured to crop the second set of plurality of images, thereby yielding a third set of plurality of images, wherein the cropping is user-defined.

Further, the software architecture includes a sixth protocol, wherein the sixth protocol is configured to apply a weight to image pixel intensities of the third set of plurality of images, thereby yielding a fourth set of plurality of images. Moreover, the software architecture includes a seventh protocol, wherein the seventh protocol is configured to perform a transformation on the fourth set of plurality of images from a signal space to a frequency space, thereby yielding transformed set of plurality of images.

The software architecture also includes an eighth protocol, wherein the eighth protocol is configured to compute a magnitude of each image of the transformed set of plurality of images, thereby yielding a set of magnitude transformed images. The software architecture next includes a ninth protocol, wherein the ninth protocol is configured to perform a coordinate transformation on the set of magnitude transformed images, thereby yielding a set of coordinate transformed images. Additionally, the software architecture includes a tenth protocol, wherein the tenth protocol is configured to quantify displacement between pairs of coordinate transformed images, thereby yielding a plurality of displacements across the set of coordinate transformed images.

Next, the software architecture includes an eleventh protocol, wherein the eleventh protocol is configured to transform the plurality of displacements into a Cartesian coordinate system, thereby yielding transformed plurality of displacements. Further, the software architecture includes a twelfth protocol, wherein the twelfth protocol is configured to compute strain rates from the transformed plurality of displacements. Additionally, the software architecture includes a thirteenth protocol, wherein the thirteenth protocol is configured to evaluate strain by integrating the strain rates.

In one or more embodiments, the reference image includes a first image, a last image, an image within the plurality of images, or a user selected image.

In at least one embodiment, the fourth protocol includes a first procedure, wherein the first procedure is configured to calculate an affine transformation of each tracked feature point to the reference image. The fourth protocol additionally includes a second procedure, wherein the second procedure is configured to apply the affine transformation to register each image to the reference image.

In some embodiments, the transformation comprises a Fourier transformation.

In some embodiments, the coordinate transformation comprises at least one of a log-polar coordinate system, polar coordinate system, or log-log coordinate system.

In some embodiments, the quantifying displacement is performed using a Fourier transformation.

Example 2

A non-transitory machine readable storage medium having a machine readable program stored therein, wherein the machine readable program, when executed on a processing system, causes the processing system to perform a method of image processing, wherein the method includes reading a plurality of images. The method additionally includes selecting a set of user defined feature points. Further, the method includes tracking the user defined feature points through the plurality of images, thereby yielding a plurality of tracked feature points. Next, the method includes registering the plurality of images to a reference image using the plurality of tracked feature points, thereby yielding a second set of plurality of images.

Moreover, the method includes cropping the second set of plurality of images, thereby yielding a third set of plurality of images, wherein the cropping is user-defined. Further, the method includes applying a weight to image pixel intensities of the third set of plurality of images, thereby yielding a fourth set of plurality of images. Next, the method includes performing a transformation on the fourth set of plurality of images from a signal space to a frequency space, thereby yielding transformed set of plurality of images.

The method also includes computing a magnitude of each image of the transformed set of plurality of images, thereby yielding a set of magnitude transformed images. Next, the method includes performing a coordinate transformation on the set of magnitude transformed images, thereby yielding a set of coordinate transformed images. Further, the method includes quantifying displacement between pairs of coordinate transformed images, thereby yielding a plurality of displacements across the set of coordinate transformed images.

Further, the method includes transforming the plurality of displacements into a Cartesian coordinate system, thereby yielding transformed plurality of displacements. Next, the method includes computing strain rates from the transformed plurality of displacements. The method also includes evaluating strain by integrating the strain rates.

In one or more embodiments, the reference image includes a first image, a last image, an image within the plurality of images, or a user selected image.

In at least one embodiment, the registering the plurality of images to the reference image using the plurality of tracked feature points, thereby yielding the second set of plurality of images includes calculating an affine transformation of each tracked feature point to the reference image. The method also includes applying the affine transformation to register each image to the reference image.

In some embodiments, the transformation comprises a Fourier transformation.

In some embodiments, the coordinate transformation comprises at least one of a log-polar coordinate system, polar coordinate system, or log-log coordinate system.

In some embodiments, the quantifying displacement is performed using a Fourier transformation.

One of ordinary skill in the art would recognize that operations are added or removed from the above method, in one or more embodiments. One of ordinary skill in the art would also recognize that the order of the operations in the above method is varied in various alternative embodiments.

FIG. 1 illustrates one example of a computing or processing node 1500 for executing the above method or the software architecture. This is not intended to suggest any limitation as to the scope of use or functionality of embodiments of the invention described herein. Regardless, the computing node 1500 is capable of being implemented and/or performing any of the functionality set forth hereinabove.

In computing node 1500 there is a computer system/server 1502, which is operational with numerous other general purpose or special purpose computing system environments or configurations. Examples of well-known computing systems, environments, and/or configurations that may be suitable for use with computer system/server 1502 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 1502 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 502 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 1502 in cloud computing node 1500 is shown in the form of a general-purpose computing device. The components of computer system/server 1502 may include, but are not limited to, one or more processors or processing units 1504, a system memory 1506, and a bus 1508 that couples various system components including system memory 1506 to processor 1504.

Bus 1508 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 1502 typically includes a variety of computer system readable media. Such media may be any available media that is accessible by computer system/server 1502, and it includes both volatile and non-volatile media, removable and non-removable media.

System memory 1506, in one embodiment, implements the above methods and the software architectures. The system memory 506 can include computer system readable media in the form of volatile memory, such as random access memory (RAM) 1510 and/or cache memory 1512. Computer system/server 1502 may further include other removable/non-removable, volatile/non-volatile computer system storage media. By way of example only, storage system 1514 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 1508 by one or more data media interfaces. As will be further depicted and described below, memory 1506 may include at least one program product having a set (e.g., at least one) of program modules that are configured to carry out the functions of various embodiments of the invention.

Program/utility 1516, having a set (at least one) of program modules 1518, may be stored in memory 1506 by way of example, and not limitation, as well as an operating system, one or more application programs, other program modules, and program data. Each of the operating system, one or more application programs, other program modules, and program data or some combination thereof, may include an implementation of a networking environment. Program modules 1518 generally carry out the functions and/or methodologies of various embodiments of the invention as described herein.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Computer system/server 1502 may also communicate with one or more external devices 1520 such as a keyboard, a pointing device, a display 1522, etc.; one or more devices that enable a user to interact with computer system/server 1502; and/or any devices (e.g., network card, modem, etc.) that enable computer system/server 1502 to communicate with one or more other computing devices. Such communication can occur via I/O interfaces 1524. Still yet, computer system/server 1502 can communicate with one or more networks such as a local area network (LAN), a general wide area network (WAN), and/or a public network (e.g., the Internet) via network adapter 1526. As depicted, network adapter 1526 communicates with the other components of computer system/server 1502 via bus 1508. It should be understood that although not shown, other hardware and/or software components could be used in conjunction with computer system/server 1502. Examples, include, but are not limited to: microcode, device drivers, redundant processing units, external disk drive arrays, RAID systems, tape drives, and data archival storage systems, etc.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, design, machine, manufacture, and composition of matter, means, methods and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

The invention claimed is:

1. A non-transitory machine-readable storage medium having a machine-readable program stored therein, wherein the machine-readable program, when executed on a processing system, causes the processing system to perform a method of image processing for echocardiogram images, wherein the method comprises:
   (a) reading a first plurality of images of a cardiac tissue;
   (b) selecting a set of user defined feature points from the first plurality of images by selecting three initial points corresponding to a left ventricular (LV) apex, a mitral annulus (MA) septal, and MA lateral positions on a first image of the plurality of images;
   (c) tracking the user defined feature points through the first plurality of images, thereby yielding a plurality of tracked feature points;
   (d) registering the first plurality of images to a reference image using the plurality of tracked feature points, thereby yielding a second plurality of images;
   (e) cropping the second plurality of images, thereby yielding a third plurality of images, wherein the cropping is user-defined;
   (f) performing a mathematical transformation on the third plurality of images from a signal space of pixel intensities to a frequency space of pixel wave numbers, thereby yielding a transformed plurality of images;
   (g) computing a magnitude of each image of the transformed plurality of images, thereby yielding a set of magnitude transformed images;
   (h) performing a coordinate transformation on the set of magnitude transformed images, thereby yielding a set of coordinate transformed images;
   (i) quantifying displacement between pairs of the set of coordinate transformed images, thereby yielding a plurality of displacements across the set of coordinate transformed images;
   (j) transforming the plurality of displacements into a Cartesian coordinate system, thereby yielding transformed plurality of displacements;
   (k) using the transformed plurality of displacements, computing average strain rates of a change in the length of the cardiac tissue; and
   (l) evaluating an average strain of a cardiac chamber of the cardiac tissue by integrating the average strain rates.

2. The non-transitory machine-readable storage medium of claim 1, wherein the reference image comprises a first image of the first plurality of images, a last image of the first plurality of images, another image within the first plurality of images, or a user selected image from the first plurality of images.

3. The non-transitory machine-readable storage medium of claim 1, wherein the registering the first plurality of images to the reference image using the plurality of tracked feature points, thereby yielding the second plurality of images comprises:
   (a) calculating an affine transformation of each tracked feature point to the reference image; and
   (b) applying the affine transformation to register each image to the reference image.

4. The non-transitory machine-readable storage medium of claim 1, wherein the mathematical transformation comprises a Fourier transformation.

5. The non-transitory machine-readable storage medium of claim 1, wherein performing the coordinate transformation on the set of magnitude transformed images includes interpolating the magnitude transformed images from an image grid onto a logarithm-scale grid.

6. The non-transitory machine-readable storage medium of claim 1, wherein quantifying displacement between pairs of the set of coordinate transformed images includes using a Fourier transformation whereby a Fourier transformation correlation plane is obtained, wherein a position of the largest value on the correlation plane corresponds to the quantifying displacement based on how far the position deviates from a center of the correlation plane.

7. A non-transitory machine-readable storage medium having a machine-readable program stored therein, wherein the machine-readable program, when executed on a processing system, causes the processing system to perform a method of image processing for echocardiogram images, wherein the method comprises:
   (a) reading a first plurality of images;
   (b) selecting a set of user defined feature points from the first plurality of images by selecting three initial points corresponding to a left ventricular (LV) apex, a mitral annulus (MA) septal, and MA lateral positions on a first image of the plurality of images;
   (c) tracking the user defined feature points through the plurality of images, thereby yielding a plurality of tracked feature points;
   (d) registering the plurality of images to a reference image using the plurality of tracked feature points, thereby yielding a second set of plurality of images, wherein the reference image is specified from within the plurality of images;
   (e) cropping the second set of plurality of images, thereby yielding a third set of plurality of images, wherein the cropping is user-defined;
   (f) performing a Fourier transformation on the third set of plurality of images from a signal space of pixel intensities to a frequency space of pixel wave numbers, thereby yielding a transformed set of plurality of images;
   (g) computing a magnitude of each image of the Fourier transformed set of plurality of images, thereby yielding a set of magnitude transformed images;
   (h) performing a coordinate transformation on the set of magnitude transformed set of plurality of images, thereby yielding a set of coordinate transformed images;
   (i) quantifying displacement between pairs of coordinate transformed images, thereby yielding a plurality of displacements across the set of coordinate transformed images;
   (j) transforming the plurality of displacements into a Cartesian coordinate system, thereby yielding transformed plurality of displacements;
   (k) computing average strain rates of a change in the length of a cardiac tissue using the transformed plurality of displacements; and
   (l) evaluating strain by integrating the average strain rates.

8. The non-transitory machine-readable storage medium of claim 7, wherein the reference image is one of a first frame of the first plurality of images, a last frame of the first plurality of images, or a user selected image from within the first plurality of images.

9. The non-transitory machine-readable storage medium of claim 7, wherein the registering the first plurality of images to the reference image using the plurality of tracked feature points, thereby yielding the second plurality of images comprises:

(a) calculating a transformation of each tracked feature point to the reference image; and
(b) applying the transformation to register each image to the reference image.

10. The non-transitory machine-readable storage medium of claim 7, wherein quantifying displacement between pairs of coordinate transformed images includes using a Fourier transformation.

* * * * *